(12) United States Patent
Barkats

(10) Patent No.: US 9,926,574 B2
(45) Date of Patent: *Mar. 27, 2018

(54) WIDESPREAD GENE DELIVERY TO MOTOR NEURONS USING PERIPHERAL INJECTION OF AAV VECTORS

(75) Inventor: Martine Barkats, Charenton le Pont (FR)

(73) Assignees: GENETHON, Evry (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 158 days.

This patent is subject to a terminal disclaimer.

(21) Appl. No.: 12/734,016

(22) PCT Filed: Oct. 3, 2008

(86) PCT No.: PCT/EP2008/063297
§ 371 (c)(1),
(2), (4) Date: May 28, 2010

(87) PCT Pub. No.: WO2009/043936
PCT Pub. Date: Apr. 9, 2009

(65) Prior Publication Data
US 2010/0240739 A1    Sep. 23, 2010

(30) Foreign Application Priority Data
Oct. 5, 2007   (EP) ..................... 07301435

(51) Int. Cl.
*C12N 15/86* (2006.01)
*A61K 48/00* (2006.01)

(52) U.S. Cl.
CPC .............. *C12N 15/86* (2013.01); *A61K 48/00* (2013.01); *C12N 2750/14143* (2013.01)

(58) Field of Classification Search
CPC ................... A61K 48/00; C12N 15/86; C12N 2750/14143
See application file for complete search history.

(56) References Cited

U.S. PATENT DOCUMENTS

| | | | |
|---|---|---|---|
| 7,465,583 B2 | 12/2008 | Samulski et al. | |
| 2003/0118556 A1* | 6/2003 | Kaspar et al. | 424/93.2 |
| 2003/0161814 A1 | 8/2003 | Wang et al. | |
| 2003/0219414 A1 | 11/2003 | Podsakoff et al. | |
| 2004/0029106 A1* | 2/2004 | Samulski et al. | 435/5 |
| 2005/0014262 A1 | 1/2005 | Gao et al. | |
| 2005/0032219 A1 | 2/2005 | Aubourg et al. | |
| 2006/0110364 A1* | 5/2006 | Harding | 424/93.2 |
| 2007/0003524 A1 | 1/2007 | Kaspar | |
| 2007/0036760 A1* | 2/2007 | Wilson et al. | 424/93.2 |
| 2009/0087413 A1 | 4/2009 | Shepard | |
| 2010/0129405 A1 | 5/2010 | Schmidt et al. | |
| 2010/0130594 A1 | 5/2010 | Barkats | |
| 2010/0221225 A1* | 9/2010 | Byrne et al. | 424/93.2 |
| 2010/0297084 A1 | 11/2010 | Bennett et al. | |

FOREIGN PATENT DOCUMENTS

| | | |
|---|---|---|
| EP | 2 019 143 | 1/2009 |
| WO | WO 03/055983 | 7/2003 |
| WO | WO 2005/033321 A2 | 4/2005 |
| WO | WO 2005/056807 A2 | 6/2005 |
| WO | WO 2005/084705 | 9/2005 |

OTHER PUBLICATIONS

Azzouz et al J Clin Invest. 2004, 114(12): 1726-1731.*
Fu et al Molecular Therapy, 2007, 16, 296-301.*
Inagaki et al Molecular Therapy, 2006, 14 (1), 45-53.*
Cearley Molecular therapy, 2006, 528-537.*
Mori et al., "Two novel adeno-associated viruses from cynomolgus monkey: pseudotyping characterization of capsid protein," Virology, vol. 330, pp. 375-383 (2004).*
Suzuki et al Acta Pediatr. Suppl. 2003, 443, 54-62.*
Walkley et al, Brain Pathol. 1998; 8(1):175-93.*
Foust et al (Nature Biotechnology, 2009, 27, 59-65.*
Schuchman EH, Chemistry and Physics of lipids 102: 179-188, 1999.*
Foust et al Nature Biotechnology, 2010, 271-276.*
Mingozzi et al Nature Review, 2011, 341-355.*
International Search Report for PCT/EP2008/063297, dated Feb. 16, 2009.
Written Opinion of the International Searching Authority for PCT/EP2008/063297, dated Feb. 16, 2009.
Fu, H. et al., "Self-Complementary Adeno-associated Virus Serotype 2 Vector: Global Distribution and Broad Dispersion of AAV-Mediated Transgene Expresssion in Mouse Brain", Molecular Therapy, vol. 8, No. 6, (Dec. 2003), pp. 911-917.
Inagaki, K. et al., "Robust Systemic Transduction with AAV9 Vectors in Mice: Efficient Global Cardiac Gene Transfer Superior to That of AAV8", Molecular Therapy, vol. 14, No. 1, (Jul. 2006), pp. 45-53.
Kasper, B.K. et al., "Retrograde Viral Delivery of IGF-1 Prolongs Survival in a Mouse ALS Model", Science, vol. 301, No. 5634, (Aug. 8, 2003), pp. 839-842.
Boulis, N.M. et al., "Adeno-associated viral vector gene expression in the adult rat spinal cord following remote vector delivery", Neurobiology of Disease, vol. 14, No. 3, (Dec. 2003), pp. 535-541.
Hollis, Edmund R. et al., "Efficient Retrograde Neuronal Transduction Utilizing Self-complementary AAV1", Molecular Therapy, vol. 16, No. 2, (Feb. 1, 2006), pp. 296-301.

(Continued)

*Primary Examiner* — Anoop K Singh
(74) *Attorney, Agent, or Firm* — Arrigo, Lee, Guttman & Mouta-Bellum LLP

(57) ABSTRACT

The present invention relates to compositions and methods, in particular to methods based on systemic injection of rAAV, for delivering genes to cells of the central nervous system in mammals, such as brain neurons or glial cells, and in particular to motor neurons or glial cells of the spinal cord The invention also relates to methods of treating motor neuron disorders in mammals by expression of therapeutic genes. The invention stems from the unexpected discovery that peripheral injection of AAV vectors leads to a bypass of the blood brain barrier and a massive infection of motor neurons. The invention may be used in any mammal, including human subjects.

18 Claims, 11 Drawing Sheets

(56) References Cited

OTHER PUBLICATIONS

Figure 1:
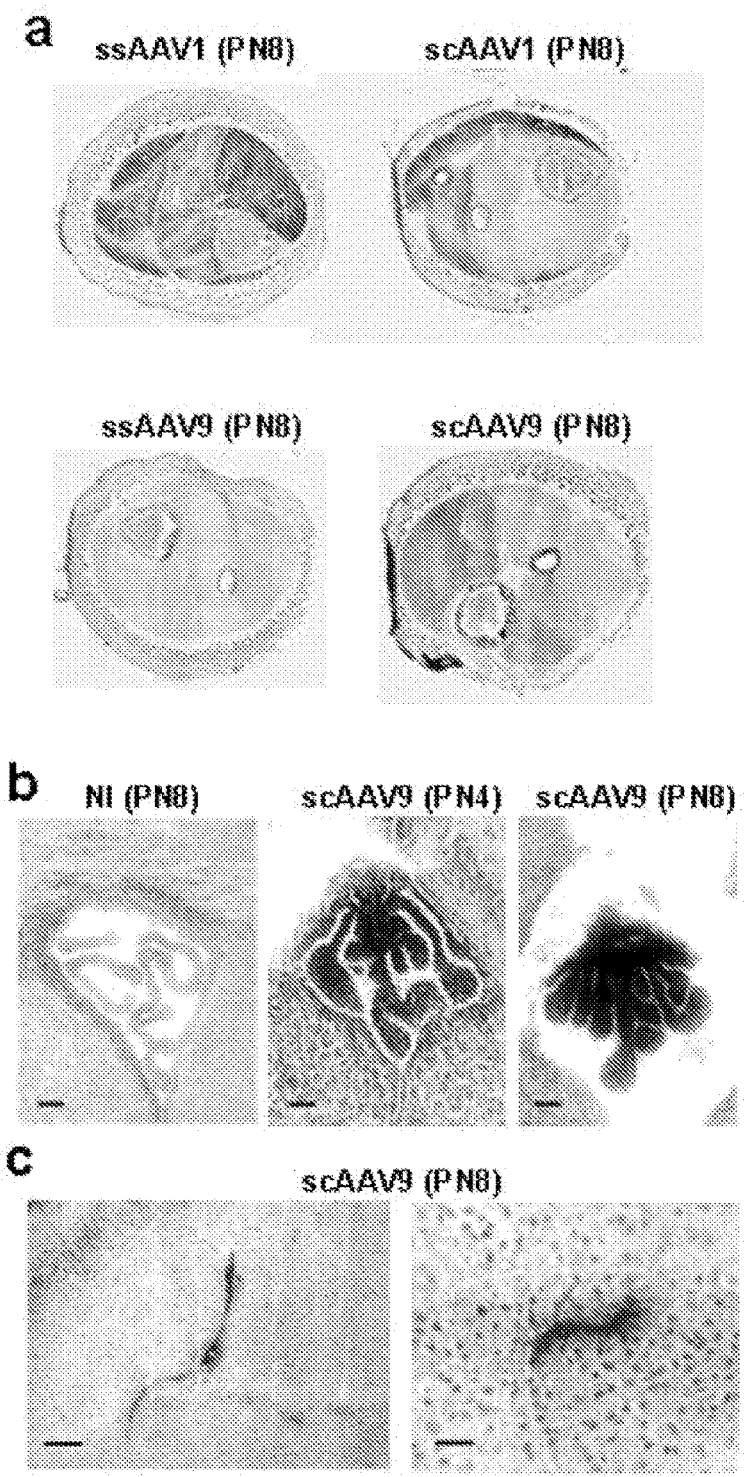

International Search Report for PCT/EP2008/059595, dated Nov. 11, 2008.
Written Opinion of the International Searching Authority for PCT/EP2008/059595, dated Nov. 11, 2008.
Broekman et al., "Complete Correction of Enzymatic Deficiency and Neurochemistry in the GM1-Gangliosidosis Mouse Brain by Neonatal Adeno-Associated Virus-Mediated Gene Delivery", www.moleculartherapy.org vol. 15, No. 1, pp. 30-37, Jan. 2007.
Mouri et al., "Oral Vaccination with a Viral Vector Containing a Beta cDNA Attenuates Age-Related a Beta Accumulation and Memory Deficits without Causing Inflammation in a Mouse Alzheimer Model", FASEB Journal, vol. 21, No. 9, Jul. 2007, pp. 2135-2148.
Passini et al., "Combination Brain and Systemic Injections of AAV Provide Maximal Functional and Survival Benefits in the Niemann-Pick Mouse", Proceedings of the National Academy of Sciences of the United States of America, vol. 104, No. 22, May 2007, pp. 9505-9510.
Carlsson et al., "Reversal of Dyskinesias in Animal Model of Parkinson's Disease by Continuous L-DOPA Delivery using rAAV Vectors", Brain (2005), No. 128, pp. 559-569.
Pirozzi et al., Intramuscular Viral Delivery of Paraplegin Rescues Peripheral Axonopathy in a Model of Hereditary Spastic Paraplegia, Journal of Clinical Investigation, vol. 116, No. 1, Jan. 2006, pp. 202-208.
Dominguez et al, "Intravenous scAAV9 delivery of a codon-optimized SMN1 sequence rescues SMA mice", Human Molecular Genetics, 2011, vol. 20, No. 4, pp. 681-693.
Rahim et al, "Intravenous administration of AAV2/9 to the fetal and neonatal mouse leads to differential targeting of CNS cell types and extensive transduction of the nervous system", The FASEB Journal, vol. 25, Oct. 2011, pp. 3505-3518.
Duque et al, "Intravenous Administration of Self-complementary AAV9 Enables Transgene Delivery to Adult Motor Neurons", Molecular Therapy, vol. 17, No. 7, Jul. 2009, pp. 1187-1196.
Foust et al, "Rescue of the spinal muscular atrophy phenotype in a mouse model by early postnatal delivery of SMN", Nature Biotechnology—Advance Online Publication, 2010 Nature America, Inc., pp. 1-6.
Foust et al, "Intravascular AAV9 preferentially targets neonatal neurons and adult astrocytes", Nature Biotechnology—Advance Online Publication, 2008 Nature Publishing Group, pp. 1-7.
Lowenstein, "Crossing the Rubicon", Nature Biotechnology, vol. 27, No. 1, Jan. 2009, pp. 42-44.
Loeb et al, "Enhanced Expression of Transgenes from Adeno-Associated Virus Vectors with the Woodchuck Hepatitis Virus Postranscriptional Regulatory Element: Implications for Gene Therapy", Human Gene Therapy 10:2295-2305, Sep. 20, 1999.
International Search Report for PCT/EP2008/059595, dated Nov. 6, 2008.
Written Opinion of the International Searching Authority for PCT/EP2008/059595, dated Nov. 6, 2008.

\* cited by examiner

US 9,926,574 B2

WIDESPREAD GENE DELIVERY TO MOTOR NEURONS USING PERIPHERAL INJECTION OF AAV VECTORS

This application is the U.S. national phase of International Application No. PCT/EP2008/063297, filed 3 Oct. 2008, which designated the U.S. and claims priority to EP Application No. 07301435.9 filed 5 Oct. 2007, the entire contents of each of which are hereby incorporated by reference.

The present invention relates to compositions and methods for delivering genes to cells of the central nervous system in mammals. The invention also relates to methods of treating motor neuron disorders in mammals by expression of therapeutic genes. The invention stems from the unexpected discovery that peripheral injection of AAV vectors leads to a bypass of the blood brain barrier and a massive infection of motor neurons, as well as other cells in the central nervous system. The invention may be used in any mammal, including human subjects.

INTRODUCTION

Motor neuron (MN) diseases, such as spinal muscular atrophy (SMA), amyotrophic lateral sclerosis (ALS) or Kennedy's disease, are neurodegenerative disorders characterised by the selective degeneration of MNs in the spinal cord, brainstem and/or motor cortex (Monani 2005; Pasinelli and Brown 2006); (MacLean, Warne et al. 1996). There is no treatment for these diseases, mostly because drug delivery to MN via systemic injections is hindered by the presence of the "blood-brain-barrier" (BBB). This anatomical and physiological barrier is formed by tight junctions between the endothelial cells of the central nervous system (CNS) capillaries and prevents easy passage of molecules between the circulation and the CNS (Scherrmann 2002). The alternative supply of MN with recombinant proteins injected directly into the CNS parenchyma is also difficult due to the invasiveness of the surgical procedure hampering a potential clinical application.

Failure of the classical pharmacology has led the scientific community to develop new therapeutic strategies based, in particular, on gene transfer technology using viral vectors. However, conventional viral vectors generally do not pass the BBB, and the first proposed gene transfer strategies included intrathecal delivery or direct injections of the vectors into the spinal cord parenchyma (Davidson, PNAS 2000) (Azzouz, Hottinger et al. 2000). However, these invasive approaches failed to produce efficient widespread CNS transduction. Injection of the viral vectors into the cerebral ventricles was also used in the aim to transduce the epithelial cells of the choroids plexus and ependyma, mediating secretion of the therapeutic proteins in the cerebrospinal fluid (CSF) and further diffusion through the CNS parenchyma (Passini and Wolfe 2001). However, diffusion of the recombinant proteins to the whole nervous tissue was far from being optimal, and again, the potential risks related to the surgical procedure is an obstacle to the clinical application of this method. An alternative non-invasive strategy was further developed using retrograde axonal transport of viral vectors to MN through intramuscular (i.m.) injections. Gene vectors such as adenovirus, adeno-associated vector (AAV) or equine-anemia viruses pseudotyped with the rabies G glycoprotein (EIAV) indeed undergo retrograde transport along the MN axons after i.m. injections, and were successfully used to transduce lower MN in experimental animals (Finiels et al., 1995; Kaspar et al., 2003; Azzouz et al., 2004). However, the clinical value of this method remains questionable due, in particular, to the large number of both injection sites and viral particles that would be needed for targeting MN in pathologies that affect most of the patient's motor units.

In order to counteract these difficulties, we tested the efficiency for MN transduction of new AAV serotypes and genomes after intramuscular (i.m.), intravenous (i.v.) and intraperitoneal (i.p.) delivery in mice. In particular, we compared the efficiency of recombinant single-stranded and self-complementary AAV vectors (ssAAV and scAAV, respectively) of serotype 1 and 9 for mediating CNS transduction in mice.

Our main results demonstrate that recombinant AAV vectors (e.g., scAAV9) are particularly efficient to transduce spinal cord MNs after i.v. delivery in mice. Furthermore, we show the feasibility of this method in a large animal model, a domestic cat model of autosomal recessive SMA similar to human SMA type III, associated to deletions of the LIX1 gene (Fyfe et al, 2006). Our method also allows to transduce other cells of the CNS, including glial cells, neurons in the hippocampus and habenular nuclei, and astrocytes. This invention thus shows, for the first time, that it is possible to transfer genes of interest to MNs after a single i.v. injection in mice, achieving broad gene delivery to the spinal cord and/or other nervous cells, therefore, offering new avenues for the treatment of MN diseases.

SUMMARY OF THE INVENTION

The present invention relates to novel compositions and methods for the delivery of therapeutic products to the CNS using recombinant AAV vectors. More specifically, the invention relates to compositions and methods for delivering genes into the motor neurons or glial cells of mammalian subjects through peripheral administration of AAV vectors.

An object of this invention more specifically relates to the use of an AAV vector comprising a gene of interest (e.g., encoding a therapeutic or diagnostic product) for the manufacture of a medicament for delivering the gene to cells in the central nervous system, particularly motor neurons or glial cells, by peripheral administration of said AAV vector to said subject.

An other object of this invention relates to the use of an AAV vector comprising a gene of interest (e.g., encoding a therapeutic or diagnostic product) for the manufacture of a medicament for delivering the gene to spinal cord motor neurons by peripheral administration of said AAV vector to said subject.

A further object of this invention resides in a method of delivering a gene to cells in the central nervous system, particularly motor neurons or glial cells, in a mammal, the method comprising administering to the mammal by peripheral route an AAV vector comprising said gene, said administration allowing infection of cells in the central nervous system, particularly motor neurons or glial cells, by said AAV vectors and thereby delivery of said gene to cells in the central nervous system, particularly motor neurons or glial cells.

An object of this invention also relates to the use of an AAV vector comprising a therapeutic gene for the manufacture of a medicament for treating a motor neuron disorder in a subject, wherein said AAV vector is administered by peripheral injection to said subject, said administration causing infection of (spinal cord) motor neurons and expression of the gene in (spinal cord) motor neurons.

Another object of this invention relates to the use of an AAV vector for the manufacture of a medicament for producing a therapeutic protein or RNA into (spinal cord) motor neurons of a subject by peripheral injection of said vector.

The invention also relates to the use of an AAV vector for delivering a gene to cells in the central nervous system, particularly motor neurons or glial cells, by crossing the blood brain barrier.

The invention also relates to a method of gene therapy across the blood brain barrier in a mammalian subject, the method comprising the peripheral administration of an AAV vector to the subject.

A further object of this invention is a method of genetically modifying cells in the central nervous system, particularly motor neurons in a mammalian subject, the method comprising peripherally administering AAV vectors to the subject.

The invention also relates to the use of an AAV vector for the manufacture of a medicament for delivering a gene to the spinal cord by peripheral administration of the AAV vector.

The invention also resides in a method of gene delivery to the spinal cord of a subject, the method comprising peripherally administering to the subject an AAV vector comprising said gene.

LEGEND TO THE FIGURES

FIG. 1. Widespread gene delivery to the neonatal mouse muscles and CNS after intramuscular AAV injection (blue: mSEAP histochemical staining). Representative cross sections of the (a) gastrocnemius muscle (b) brain ($3^{rd}$ ventricle) and (c) spinal cord at 3 days (PN4) or 7 days (PN8) after injection of ss- or scAAV1 or AAV9.

NI: non-injected; PN4, post-natal 4; PN8, post-natal 8; ss, single-strand; sc: self-complementary. Scale bar (b, c) 100 μm.

Figure 2:
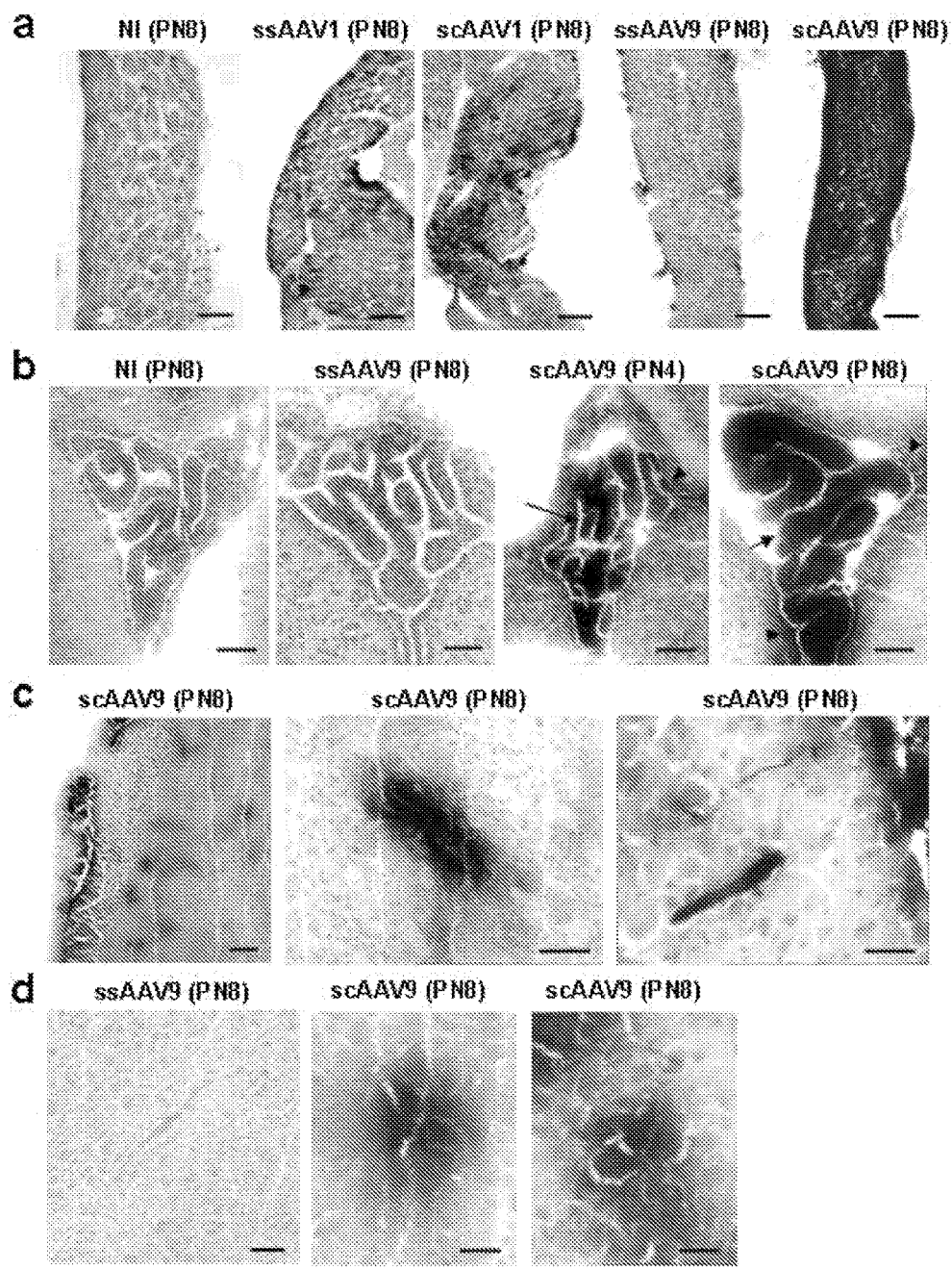

FIG. 2. Widespread gene delivery to the neonatal mouse muscles and CNS after intraperitoneal AAV injection (blue: mSEAP histochemical staining). Representative tissue sections of the (a) diaphragm muscle (b) cerebral $3^{rd}$ ventricle (arrows: mSEAP expressing choroids plexus cells; arrowheads: ependymal cells) (c) CNS parenchyma (arrows: neuronal cells).

NI: non-injected; PN4, post-natal 4; PN8, post-natal 8; ss, single-strand; sc: self-complementary. Scale bar (a, b, c) 100 μm; (d) 40 μm.

Figure 3:
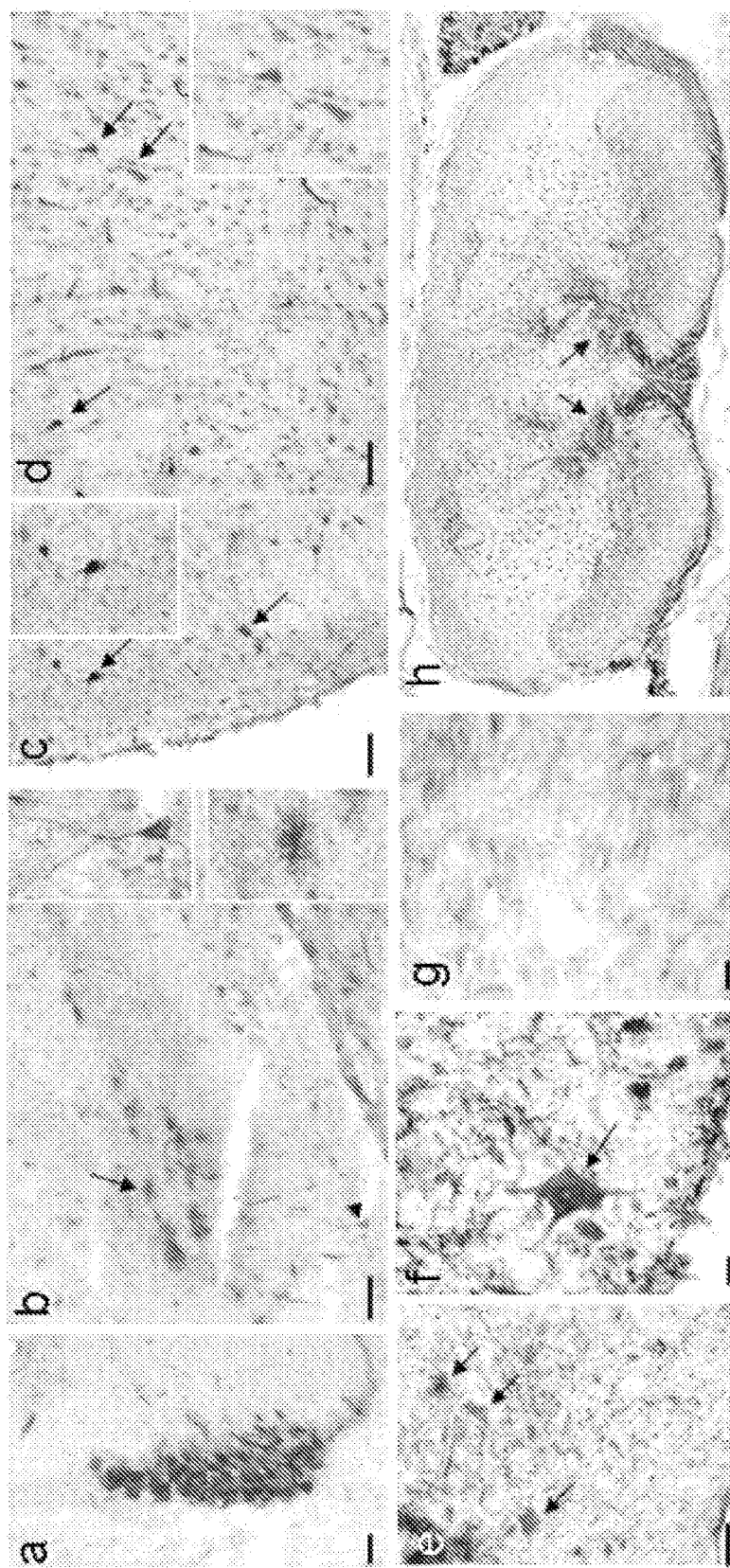

FIG. 3. Intraperitoneal delivery of self-complementary AA9-GFP mediates CNS transduction in neonatal mice. Representative brain and spinal cord cross sections treated for GFP immunohistochemistry 7 days after AAV delivery. Transgene expression was detected in (a) the choroids plexus epithelial cells (b) hippocampal cells with a neuronal (arrowhead and top box) and glial (arrow and bottom box) morphology (c) cells of the entorhinal cortex (arrows indicate cells with a typical neuronal morphology) (d, e) cells of the spinal cord (the arrow indicates a GFP-labelled cell with a motor neuron morphology) and (f) sensory fibers in the cervical spinal cord. Scale bar 40 μm.

Figure 4:
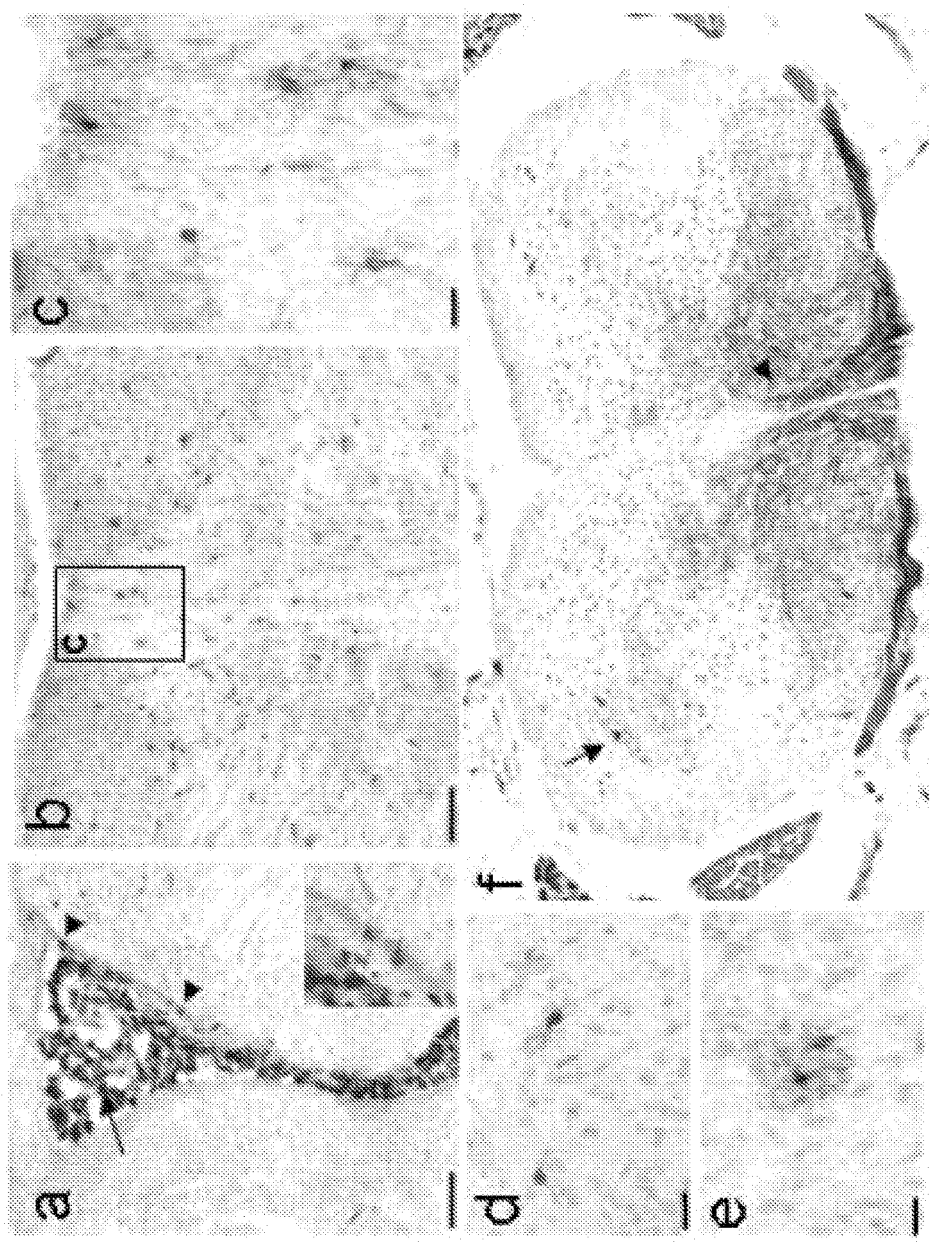

FIG. 4. Intramuscular delivery of self-complementary AAV9 vectors allows transduction of CNS cells in neonatal mice. Brain and spinal cord histological sections were treated with GFP immunohistochemistry 7 days after AAV injection. Transgene expression was detected in (a) the epithelial cells of the choroids plexus (arrow) and the ependyma (arrowheads) (b,c) neural cells of the septum and (d, e) of the entorhinal cortex and (f) the corticospinal tract at the level of the pyramidal decussation in the cervical spinal cord (arrows). Scale bar 20 μpm.

Figure 5:
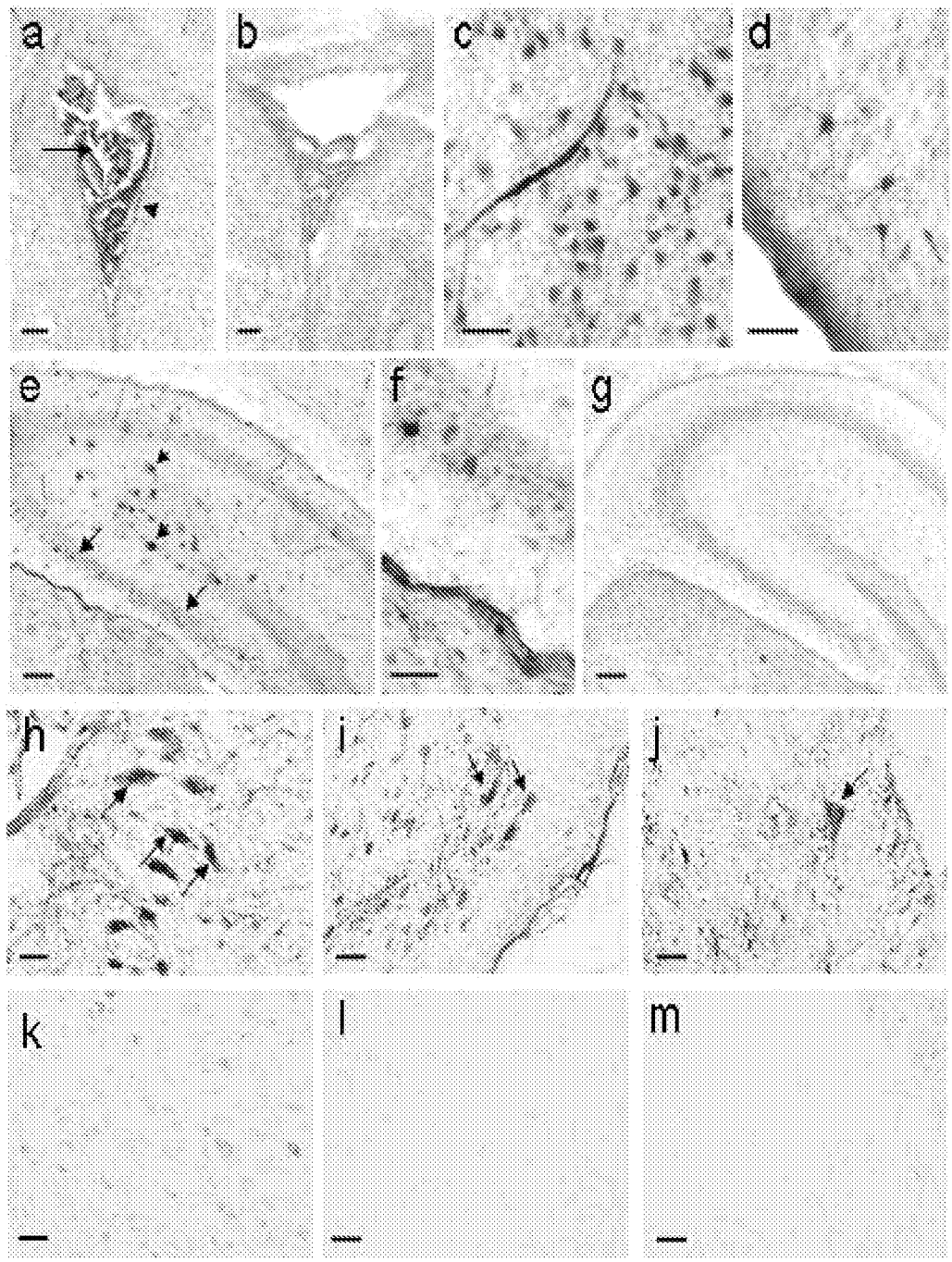

FIG. 5. Intravenous delivery of self-complementary AAV9 vectors mediate GFP expression in the CNS of neonatal mice. Representative photomicrographs of brain and spinal cord histological sections treated for GFP immunostaining 7 days after AAV injection. GFP-positive cells were detected in (a) the epithelial cells of the choroids plexus (arrow) and the ependyma (arrowheads) (c) brain blood vessels (d,f) hippocampal cells with a neuronal (arrow) and glial (arrowhead) morphology (g) neuron-like cells of the entorhinal cortex. Many motor neuron-like cell bodies (arrows) and fibres (arrowheads) were efficiently transduced throughout the spinal cord at the (h) cervical (i) thoracic and (j) lumbar levels. No staining was observed in the CNS of uninjected mice as shown in representative sections from (b) the 3rd ventricle or (e) the hippocampus or (k-m) the spinal cord. Scale bar (a, b) 100 μm, (c, d, f) 40 μpm, (e, g) 100 μpm, (h-m) 20 μm.

Figure 6:
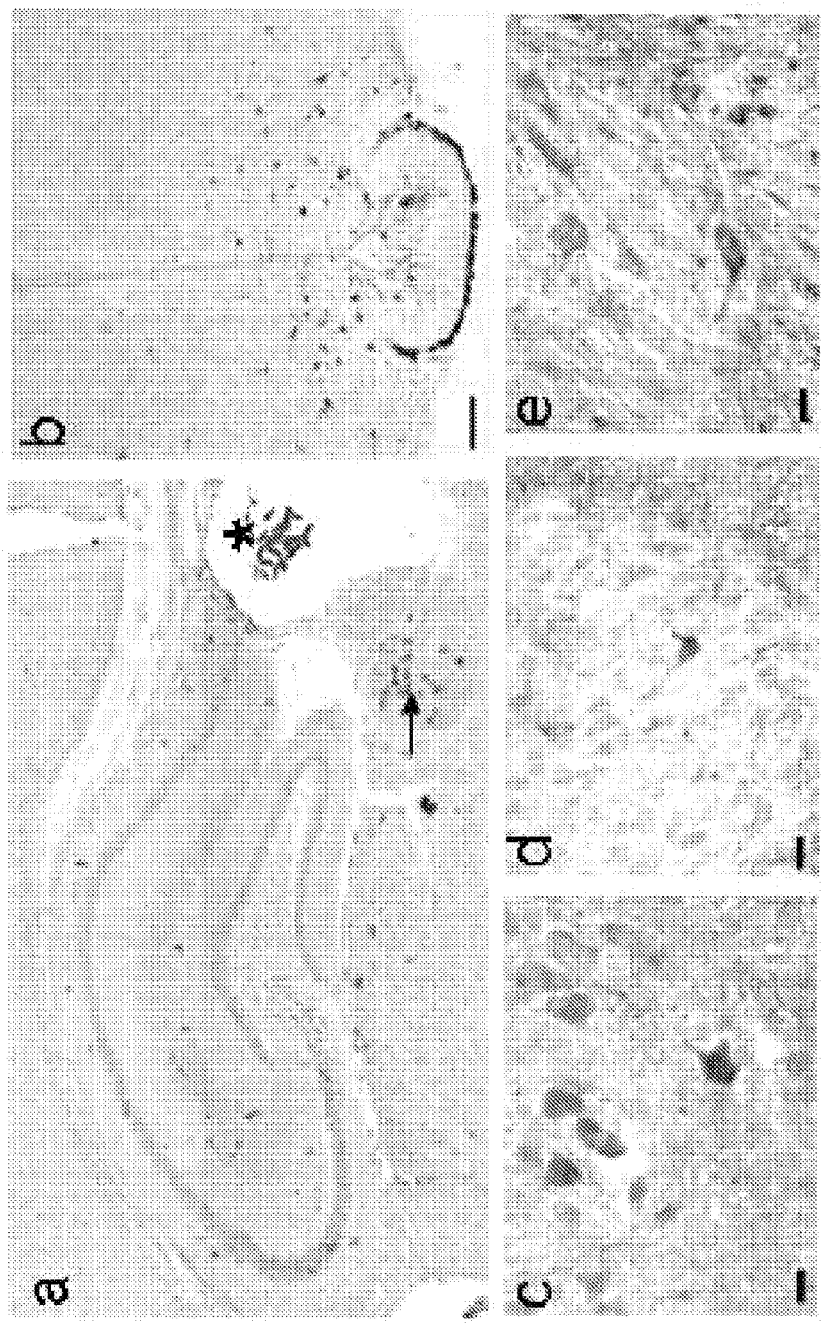

FIG. 6. GFP-expressing single-stranded AAV9 vectors mediate transgene expression in the CNS of neonatal mice. Representative photomicrographs of brain and spinal cord sections from neonatal mice treated for GFP-immunohistochemistry 3 weeks after i.v. injection of ssAAV9 vectors. GFP-positive cells in (a) the choroids plexus (asterisk), the hippocampus (arrowhead and box) and the habenular nucleus (arrow) (b) the median eminence and (c-e) motor neuron-like cells in the ventral spinal cord. Scale bar panels b: 100 μm; c, d, e: 20 μpm.

Figure 7:
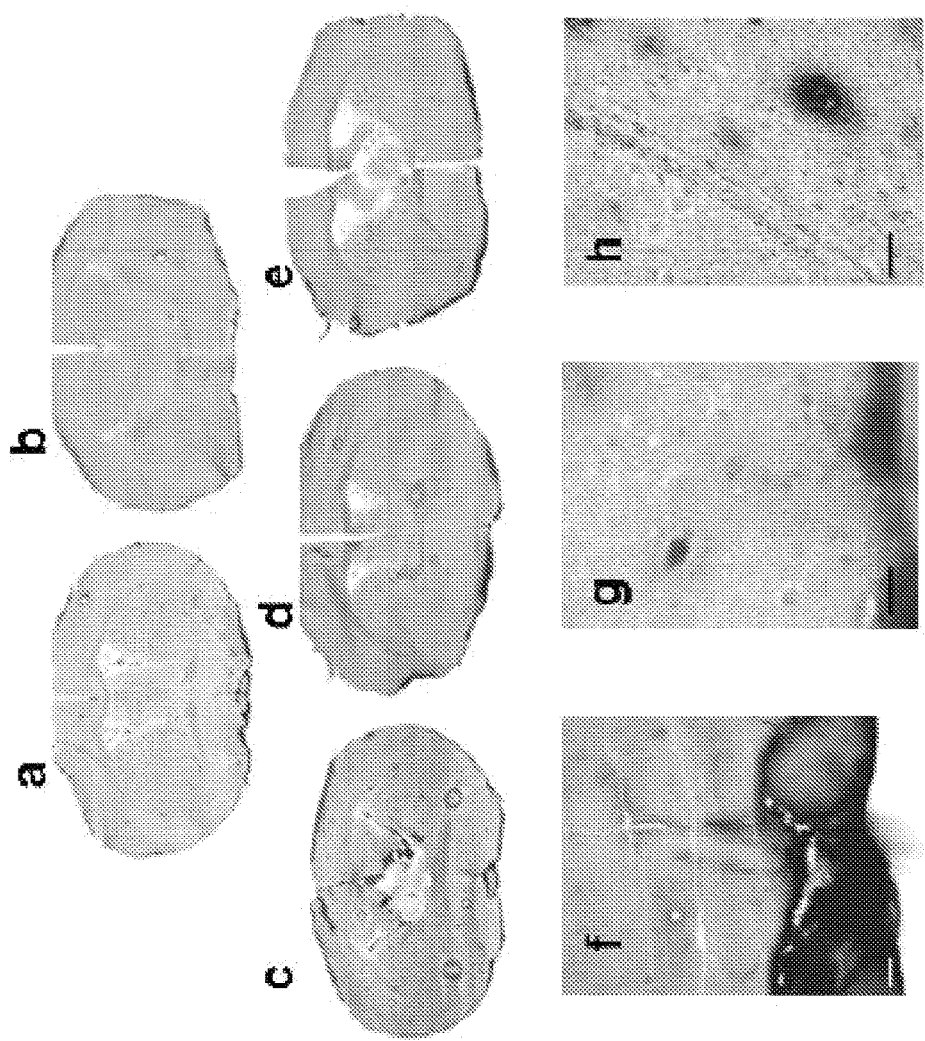

FIG. 7. Recombinant AAV9 vectors mediate transgene expression in the adult mouse CNS. Representative coronal brain sections from adult C57bl6 mice 4 weeks after intravenous delivery of $3\times10^{11}$ (b) or $1\times10^{12}$ (c-h) vector genome of mSEAP-expressing scAAV9 (a,c), ssAAV9 (b), scAAV1 (d) and ssAAV1 (e); Scale bar panels g, h, j: 100 μm; panels i, k, l: 20 μm.

Figure 8:
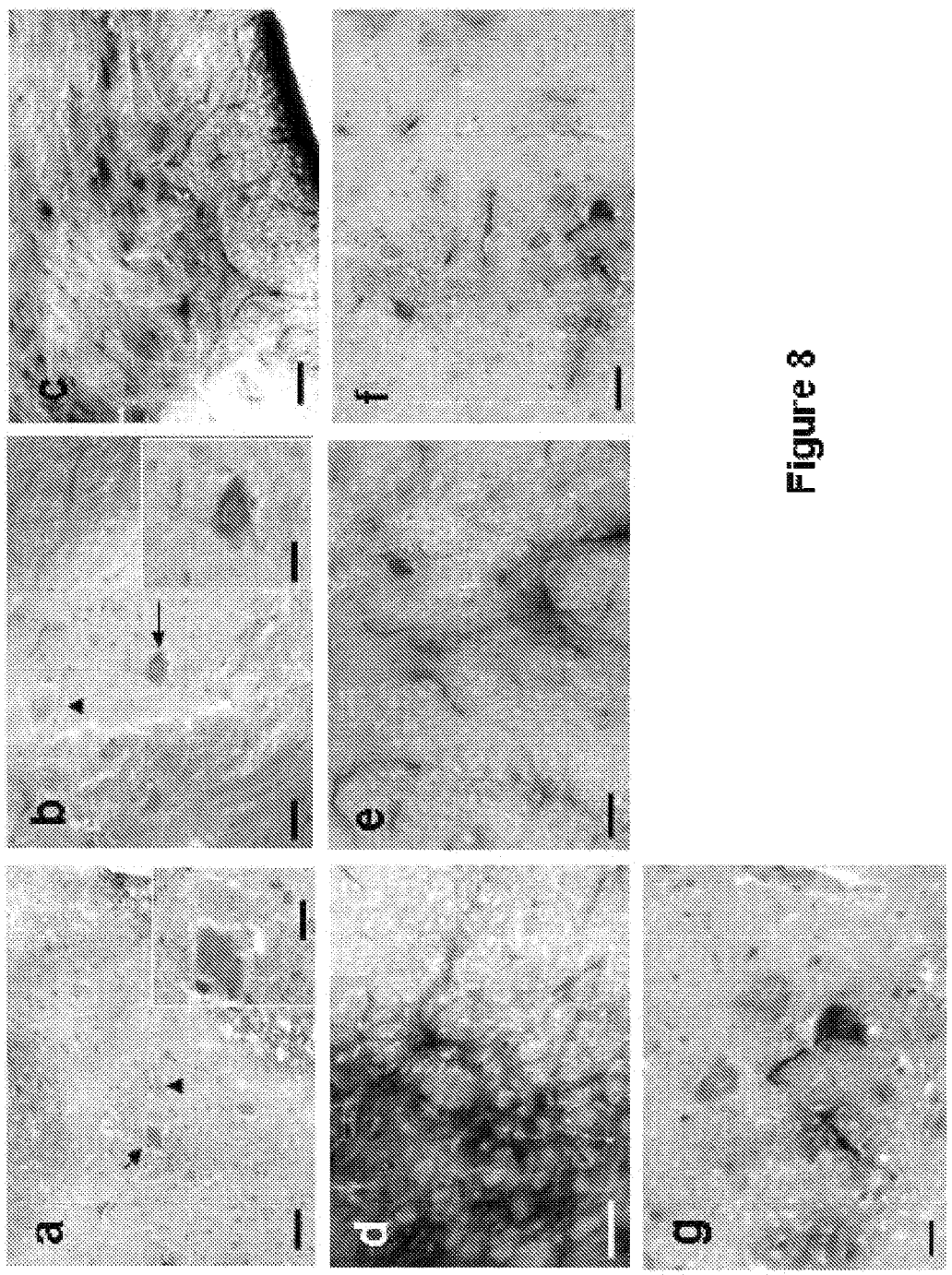

FIG. 8. Intravenously injected recombinant AAV9 vectors mediate transgene expression in the spinal cord of adult mice. Representative transversal spinal cord sections from adult C57bl6 mice 4 weeks after intravenous delivery of $1\times10^{12}$ vector genome of mSEAP-expressing ssAAV9 (a,b), scAAV9 (c,g). Scale bars (a,b,e): 40 μm, boxes: 20 μm; (c,d): 100 μm; (f): 50 μm; (g): 20 μm.

Figure 9:
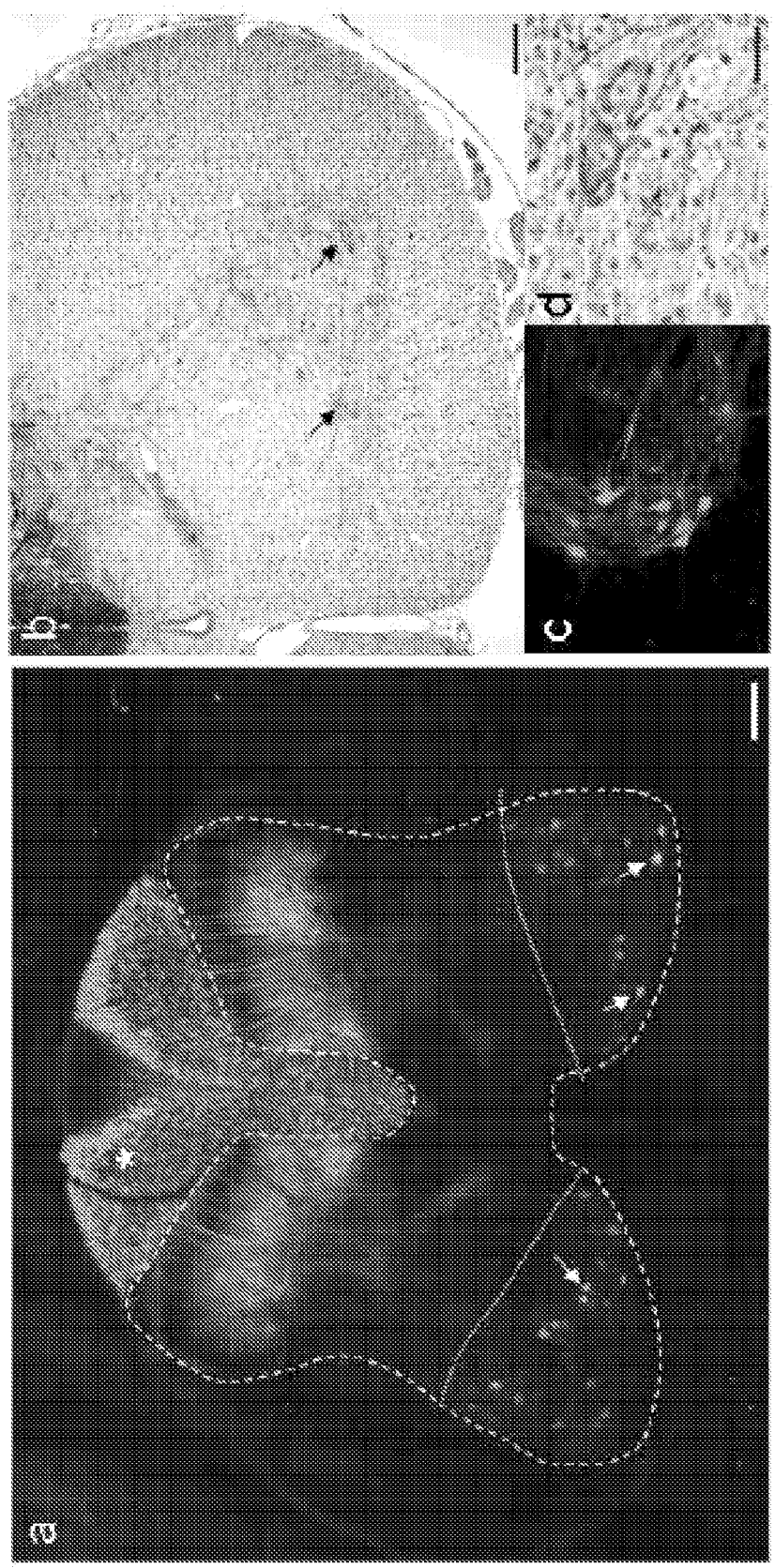

FIG. 9. Intravenous injection of AAV9-GFP in LIX-1 cats mediates transgene expression throughout the spinal cord. Representative transversal spinal cord sections from a 2 days-old LIX1 heterozygous cat were observed using laser scanning confocal microscopy (FIG. 9*a,c*) or treated for GFP immunohistochemistry (FIG. 9*b,d*) 10 days after injection of GFP-expressing scAAV9 into the jugular vein.

Scale bars (a): 200 μm; (b, d): 50 μm; (c): 100 μm.

Figure 10:
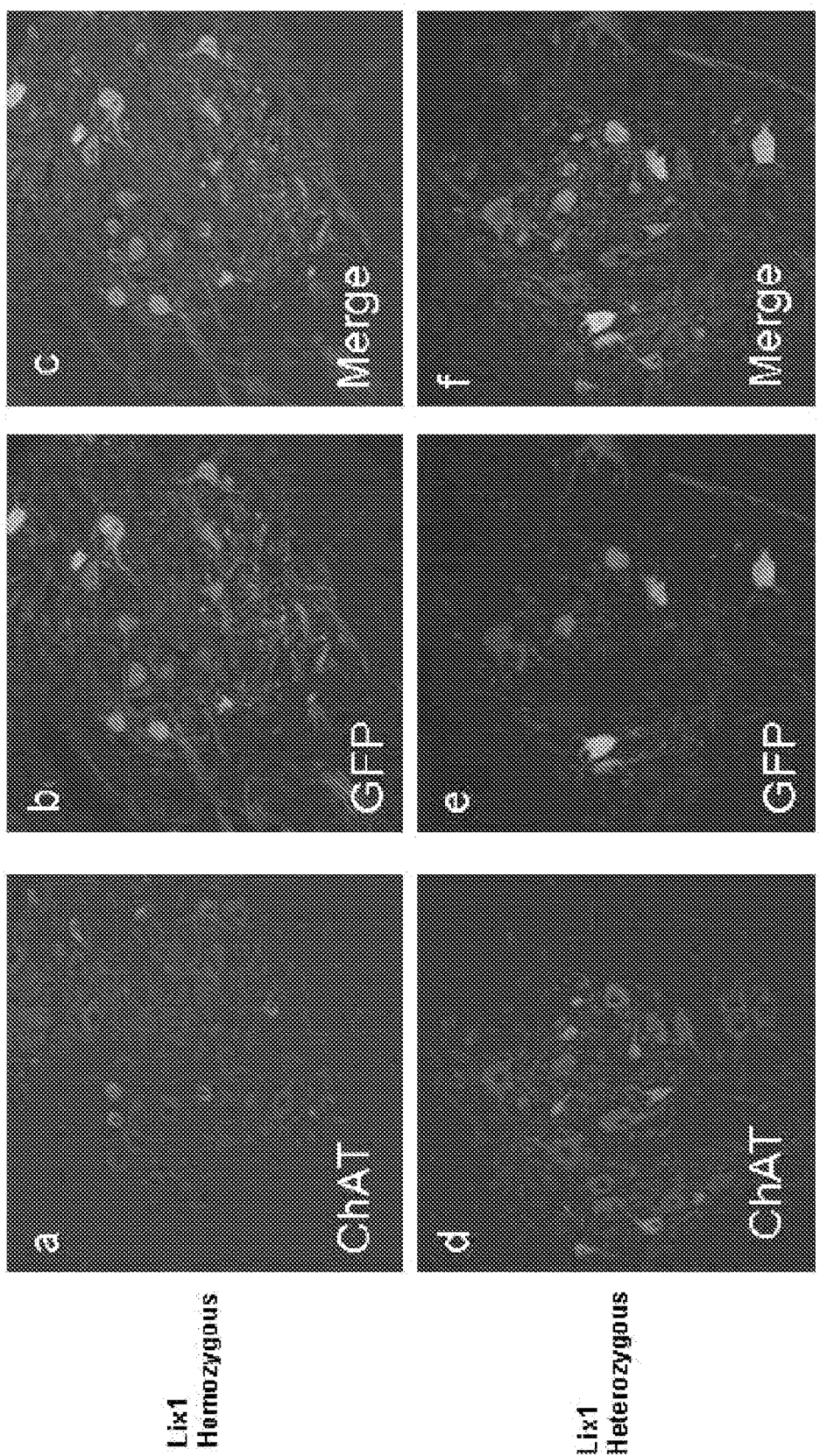

FIG. 10. Intravenous injection of GFP expressing AAV9 (1.5×10+12 vector genome-containing particles of scAAV9-CMV-eGFP) in LIX-1 cats mediates transgene expression in motor neurons. A double-immunostaining analysis using antibodies against GFP and choline acetyl transferase (ChAT) showed that, in both SMA-affected (a-c) and non-affected kitten (d-f), a significant part of the GFP-positive cells were motor neurons.

Figure 11:
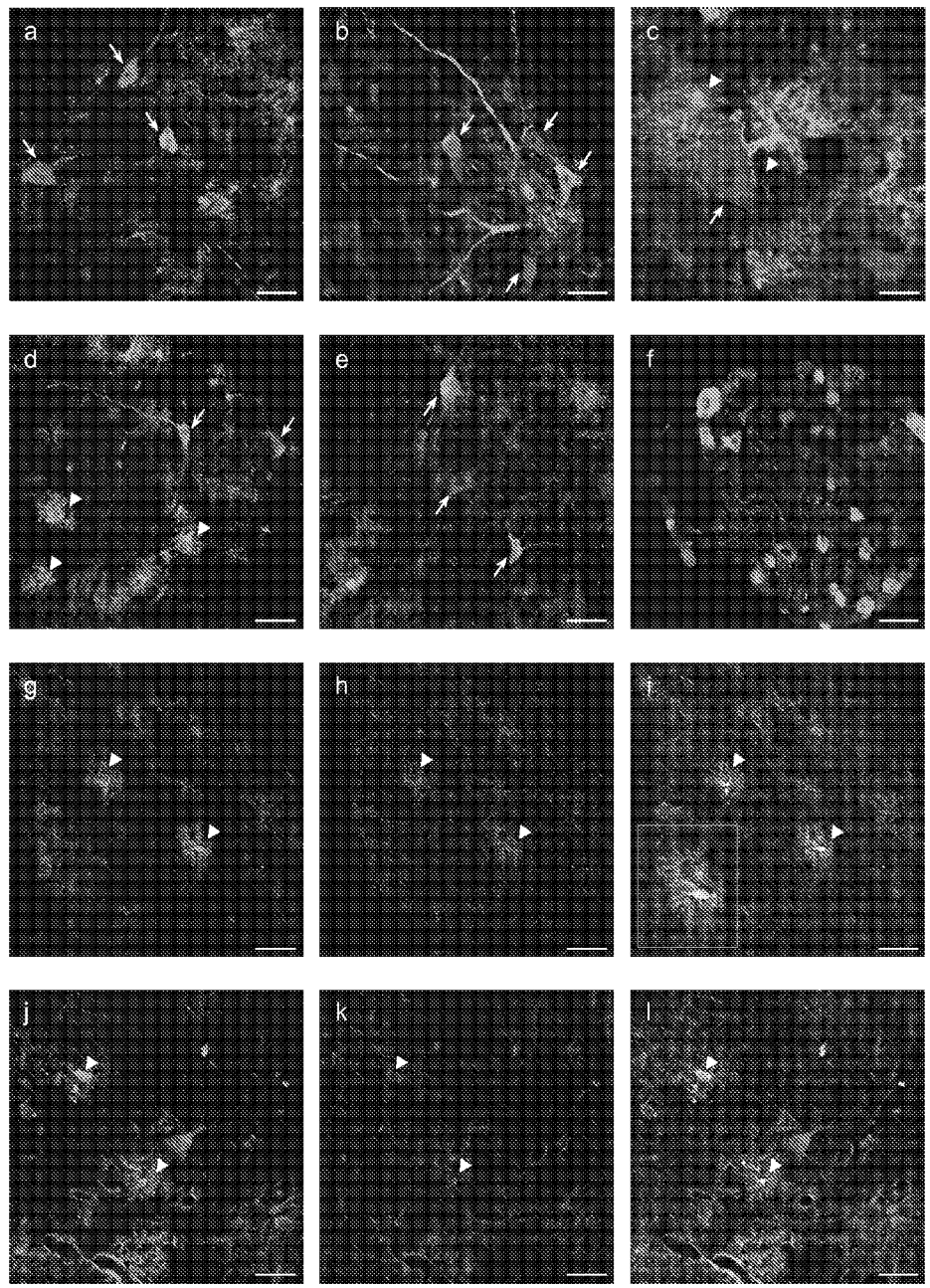

FIG. 11. Widespread spinal cord transduction is mediated by i.v. delivery of highly concentrated scAAV9 in adult mice.

High GFP expression in neuronal (arrows) and glial (arrowheads) cells in (a-c) cervical and (d,e) lumbar spinal cord (f) dorsal root ganglion sections treated for GFP-immunostaining 4 weeks after i.v. injection of $2\times10^{12}$ vg scAAV9. (g-l) Double immunofluorescence analysis for (g, j) GFP and (h, k) GFAP (glial fibrillary acidic protein, a marker of astrocytes, red) shows GFP expression in some astrocytes (arrowheads indicate double-labeled cells). (i, l) Merge. Scale bars (a, b, d-l): 50 μm, (c): 20 μm.

DETAILED DESCRIPTION OF THE INVENTION

Widespread gene delivery to the spinal cord is an important challenge for the treatment of motor neuron (MN) diseases such as spinal muscular atrophy (SMA) or amyotrophic lateral sclerosis (ALS). Here, we describe a new gene transfer methodology that allows efficient MN transduction after a single peripheral injection of recombinant AAV vectors. We injected recombinant single strand (ss) and self-complementary (sc) AAV vectors of serotype 1 and 9 intraperitonealy, intramuscularly or intravenously (i.v.) in neonatal or adult mice and analyzed transgene expression in the central nervous system (CNS). Both recombinant ss- and scAAV9 vectors were found to target neural and epithelial brain cells and, importantly, motor neurons and glial cells in the spinal cord. The dorsal sensory fibers and the dorsal root ganglions also appeared highly transduced. The most impressive transduction efficacy was obtained with i.v. injected scAAV9 vectors. We further confirmed the ability of i.v. injected scAAV9 to bypass the blood-brain barrier and transduce lower motor neurons in a feline model of SMA. This strategy represents the first non invasive procedure that achieves widespread transgene delivery to the spinal cord, offering new avenues for the treatment of MN diseases.
AAV Vectors Within the context of the present invention, the term "AAV vector" designates any vector which comprises or derives from components of AAV and is suitable to infect mammalian cells, preferably human cells. The term AAV vector typically designates an AAV type viral particle (or virion) comprising at least a nucleic acid molecule encoding a therapeutic protein. As will be discussed below, the AAV may be derived from various serotypes, including combinations of serotypes (i.e., "pseudotyped" AAV) or from various genomes (e.g. single-stranded or self-complementary). In addition, the AAV vector may be replication defective and/or targeted.

Adeno-associated virus (AAV) is a dependent parvovirus, of approximately twenty nanometers in size. Like other parvoviruses, AAV is a single-stranded, non-enveloped DNA virus, having a genome of about 5000 nucleotides in length, containing two open reading frames. The left-hand open reading frame codes for the proteins responsible for replication (Rep), while the right-hand open reading frame encodes the structural proteins of the capsid (Cap). The open reading frames are flanked by two ITR sequences, which serve as the origin of replication of the viral genome. Furthermore, the genome also contains a packaging sequence, allowing packaging of the viral genome into an AAV capsid.

AAV requires co-helper functions (which may be provided e.g. by an adenovirus, or by suitable packaging cells or helper plasmids) to undergo a productive infection in cultured cells. In the absence of such helper functions, the AAV virions essentially enter the cells, migrate to the nucleus as a single-stranded DNA molecule, and integrate into the cells' genome. AAV has a broad host range for infectivity, including human cells, is ubiquitous in humans, and is completely non-pathogenic.

AAV vectors have been designed, produced and used to mediate gene delivery in human subjects, including for therapeutic purposes. Clinical trials are presently ongoing in various countries using AAV vectors. Typically, AAV vectors for use in gene transfer comprise a replication defective AAV genome lacking functional Rep and Cap coding viral sequences. Such replication defective AAV vectors more preferably lack most or all of the Rep and Cap coding sequences, and essentially retain one or two AAV ITR sequences and a packaging sequence.

Methods of producing such AAV vectors have been disclosed in the literature, including using packaging cells, auxiliary viruses or plasmids, and/or baculovirus systems (Samulski et al., (1989) J. Virology 63, 3822; Xiao et al., (1998) J. Virology 72, 2224; Inoue et al., (1998) J. Virol. 72, 7024; WO98/22607; WO2005/072364). Methods of producing pseudotyped AAV vectors have also been reported (e.g., WO00/28004), as well as various modifications or formulations of AAV vectors, to reduce their immunogenicity upon in vivo administration (see e.g., WO01/23001; WO00/73316; WO04/112727; WO05/005610; WO99/06562).

AAV vectors may be prepared or derived from various serotypes of AAVs, which may be even mixed together or with other types of viruses to produce chimeric (e.g. pseudotyped) AAV viruses.

In a particular embodiment, the AAV vector for use in the present invention is derived from a human AAV virus.

Such a human AAV (capsid and ITR) may be derived from any known serotype, e.g. from any one of serotypes 1-11, preferably from AAV2, AAV4, AAV6, AAV8 and AAV9, more preferably from AAV6, AAV8 and AAV9, even more preferably from AAV9. Specific examples of such AAV vectors are vectors comprising an AAV2-derived genome (a nucleic acid molecule comprising an AAV2-derived ITR and an AAV2-derived packaging sequence, operatively linked to a nucleic acid encoding a therapeutic protein, preferably two AAV2-derived ITR flanking an AAV2-derived packaging sequence and a nucleic acid encoding a therapeutic protein) in an AAV2-derived capsid; vectors comprising an AAV4-derived genome in an AAV4-derived capsid; vectors comprising an AAV6-derived genome in an AAV6-derived capsid; vectors comprising an AAV8-derived genome in an AAV8-derived capsid; vectors comprising an AAV9-derived genome in an AAV9-derived capsid In another particular embodiment, the AAV vector is a pseudotyped AAV vector, i.e. comprises sequences or components originating from at least two distinct AAV serotypes. In a particular embodiment, the pseudotyped AAV vector comprises an AAV genome derived from one AAV serotype (for example AAV2), and a capsid derived at least in part from a distinct AAV serotype. Specific examples of such pseudotyped AAV vectors include, without limitation, vectors comprising an AAV2-derived genome in an AAV4-derived capsid; or vectors comprising an AAV2-derived genome in an AAV6-derived capsid; or vectors comprising an AAV2-derived genome in an AAV8-derived capsid; or vectors comprising an AAV2-derived genome in an AAV9-derived capsid;

In a further particular embodiment, which may be combined with any of the above embodiments, the AAV vector may comprise a modified capsid, including proteins or peptides of non viral origin or structurally modified, to alter the tropism of the vector. As a particular example, the capsid may include a ligand of a particular receptor, or a receptor of a particular ligand, to target the vector towards cell type(s) expressing said receptor or ligand, respectively.

In the AAV vectors used in the present invention, the AAV genome may be either a single stranded nucleic acid or a double stranded, self complementary nucleic acid (McCarty et al., Gene Therapy, 2001), more preferably a self complementary nucleic acid.

As discussed above, the AAV-derived genome comprises a nucleic acid encoding a therapeutic protein. Typically, the nucleic acid also comprises regulatory sequences allowing expression and, preferably, secretion of the encoded protein, such as e.g., a promoter, enhancer, polyadenylation signal, internal ribosome entry sites (IRES), sequences encoding protein transduction domains (PTD), and the like. In this regard, the nucleic acid most preferably comprises a promoter region, operably linked to the coding sequence, to cause or improve expression of the therapeutic protein in infected cells. Such a promoter may be ubiquitous, tissue-specific, strong, weak, regulated, chimeric, etc., to allow efficient and suitable production of the protein in the infected tissue. The promoter may be homologous to the encoded protein, or heterologous, including cellular, viral, fungal, plant or synthetic promoters. Most preferred promoters for use in the present invention shall be functional in nervous cells, particularly in human cells, more preferably in motor neurons. Examples of such regulated promoters include, without limitation, Tet on/off element-containing promoters, rapamycin-inducible promoters and metallothionein promoters. Examples of promoters specific for the motor neurons include the promoter of the Calcitonin Gene-Related Peptide (CGRP), a known motor neuron-derived factor. Other promoters functional in motor neurons include the promoters of Choline Acetyl Transferase (ChAT), Neuron Specific Enolase (NSE), Synapsin, or ubiquitous promoters including Neuron Specific Silencer Elements (NRSE). Examples of ubiquitous promoters include viral promoters, particularly the CMV promoter, the RSV promoter, the SV40 promoter, etc. and cellular promoters such as the PGK (phosphoglycerate kinase) promoter.

In a preferred embodiment, the nucleic acid comprises a leader sequence allowing secretion of the encoded protein. Fusion of the transgene of interest with a sequence encoding a secretion signal peptide (usually located at the N-terminal of secreted polypeptides) will allow the production of the therapeutic protein in a form that can be secreted from the transduced cell into the CSF. Examples of such signal peptides include the albumin, the β-glucuronidase, the alkaline protease or the fibronectin secretory signal peptides.

According to another specific embodiment, the transgene is fused with PTD sequences, such as the Tat or VP22 sequences, in order to cause or improve secretion of the therapeutic protein from the transduced cells and re-uptake by neighbour ones.

In a particular embodiment the nucleic acid comprises, operably linker, a promoter and a leader sequence, to allow expression and secretion of the encoded protein.

In a further particular embodiment, the nucleic acid comprises, operably linker, a promoter, a leader sequence and a PTD sequence, to allow expression and secretion of the encoded protein.

In a most preferred embodiment, the promoter is specific or functional in motor neurons, i.e., allows (preferential) expression of the transgene in said cells.

As discussed above, the AAV vectors may be produced by techniques known per se in the art, as further illustrated in the examples.

Peripheral Administration

The invention is based on the unexpected discovery that effective and widespread expression of genes into motor neurons or glial cells can be achieved with non-invasive techniques, through peripheral administration of AAV vectors. Such peripheral administration includes, without limitation, any administration route which does not imply direct injection into the brain. More particularly, peripheral administration comprises systemic injections, such as intramuscular (i.m.), intravenous (i.v.), intraperitoneal (i.p.), intra-arterial, sub-cutaneous or transdermic injections. Peripheral administration also includes oral administration of AAV vectors (WO96/40954), delivery using implants (WO01/91803), or administration by instillation through the respiratory system, e.g., using sprays, aerosols or any other appropriate formulations.

Most preferred peripheral administration includes peripheral injection, in particular systemic injection, most preferably i.m., i.p. or i.v. injection.

The doses of AAV vectors may be easily adapted by the skilled artisan, e.g., depending on the disease condition, the subject, the treatment schedule, etc. Typically, from $10^9$ to $10^{14}$ viral genomes (transducing units) are administered per dose in mice, preferably from about $10^{11}$ to $10^{13}$.

Typically, the doses of AAV vectors to be administered in humans may range from $10^{11}$ to $10^{17}$ viral genomes, preferably from $10^{13}$ to $10^{16}$.

A preferred effective dose within the context of this invention is a dose allowing an optimal transduction of the spinal cord cells (motor neurons and/or glial cells).

The AAV vector may be administered in any suitable form, either as a liquid solution or suspension, as a solid form suitable for solution or suspension in liquid prior to injection, as a gel or as an emulsion. The AAV vectors are typically formulated with any appropriate and pharmaceutically acceptable excipient, carrier, adjuvant, diluent, etc. For injection, the excipient may be a liquid, isotonic solution, buffer, such as a sterile and pyrogen-free water or a sterile and pyrogen-free phosphate-buffered saline solution. For inhalation, the excipient may be in particulate form.

The AAV vectors are typically administered in a "therapeutically-effective" amount, i.e., an amount that is sufficient to alleviate (e.g., decrease, reduce) at least one of the symptoms associated with the disease state, or to provide improvement in the condition of the subject. It should be pointed out that repeated administrations may be performed, if required, using either the same or different peripheral administration route and/or the same or distinct AAV serotypes.

The inventors have shown for the first time that AAV vectors, in particular scAAV vectors, administered peripherally cross the blood brain barrier and cause substantial infection of CNS cells. This effect is obtained without the need of using blood-brain barrier disrupting agents. Hyperthermia, mannitol, bradykinin and NS1619 are illustrative blood-brain barrier disrupting agents.

Accordingly, in a particular embodiment, the invention relates to an use or method as defined above, comprising peripheral administration of an AAV vector, preferably a scAAV vector, more preferably a scAAV9 vector, wherein no blood-brain barrier disrupting agent is implemented. Furthermore, the invention relates to an use or method as defined above, wherein no mannitol is injected to the subject.

Alternatively, in another particular embodiment, the invention relates to an use or method as defined above, further comprising disruption of the blood-brain barrier with a blood-brain barrier disrupting agent or process, to further increase the crossing of the scAAV vectors implemented in the present invention through the blood-brain barrier.

Motor Neuron Disorder

The invention shows, for the first time, that AAV vectors administered peripherally cross the blood brain barrier and cause substantial infection of CNS cells, particularly of motor neurons throughout the spinal cord. The results presented show that infection is effective from the cervical segment to the lumbar segment of the spinal cord, thereby providing a widespread gene delivery into motor neurons.

The invention may be used to treat a variety of disorders through delivery of a therapeutic product into CNS cells including the motor neurons. The therapeutic product may be any protein, peptide or RNA that may alleviate or reduce symptoms that result from an absence or defect in a protein in a cell or subject or that otherwise confers a benefit to a subject. Examples of therapeutic proteins include growth factors, cytokines, hormones, neurotransmitters, enzymes, anti-apoptotic factors, angiogenic factors, and any protein known to be mutated in pathological disorders such as the "survival of motor neuron" protein (SMN). Examples of therapeutic RNA include antisense RNA or RNAi targeting messenger RNAs coding for proteins having a therapeutic interest in any of the diseases mentioned herein below. For example, an RNAi targeting the superoxide dismutase enzyme may be coded by an AAV vector as defined above, in view of the treatment of ALS.

Depending on the therapeutic product, the invention can be used to treat various diseases, including any disease which may be treated or prevented by expressing therapeutic proteins into nervous tissue. Such diseases include CNS disorders, preferably selected from neurodegenerative diseases, neuromuscular diseases, lysosomal diseases, trauma, bone marrow injuries, pain (including neuropathic pain), cancers of the nervous system, demyelinating diseases, autoimmune diseases of the nervous system, neurotoxic syndromes, sleeping disorders.

Specific examples of diseases include Alzheimer's Disease, Parkinson's Disease, Huntington's Disease, Tourette Syndrome, schizophrenia, Sly disease, Hunter's disease, dementia, paranoia, obsessive compulsive disorder, learning disabilities, amyotrophic lateral sclerosis, spinal muscular atrophy, Charcot-Marie Tooth disease, spinocerebellar ataxia, spastic paraplegia, Kennedy's disease, glioblastoma, neuroblastoma, autism, Gaucher's disease, Hurler's disease, Krabbe's disease and altered behaviors (e. g., disorders in sleeping, perception or cognition).

The invention may be used in any mammalian, particularly in human subjects, including adults, for preventive or curative treatment.

The invention can also be used in diagnostic methods, to detect the status or activity or growth of motor neurons in mammalian subjects. For such indications, the vector typically comprises a detectable gene (fluorescent, luminescent, etc.) and is used as a marker.

The invention can also be used in animal subjects, e.g., to assist in the research of candidate drugs for treating CNS disorders and/or to understand the mechanisms of motor neuron growth, differentiation, activity, etc.

Further aspects and advantages of the present inventions will be disclosed in the following experimental section, which shall be considered as illustrative only, and not limiting the scope of this application.

EXAMPLES

Material and Methods

Animals. Pregnant and adult (six to eight week old, female) C57Bl/6 mice were purchased from Charles River Laboratories (Les Oncins, France). Neonates were injected on the day of birth (post-natal 1, PN1). SMA cat breeders (heterozygous and affected animals) were obtained from Dr. Fyfe (Laboratory of Comparative Medical Genetics, Mich., US) and housed in the Center of Boisbonne at the Nantes Veterinary School. Genotyping of SMA kittens was performed as described previously (Fyfe, Menotti-Raymond et al. 2006). Experiments were approved by the regional ethic committee (CREEA).

All animal experiments were carried out according to the European guidelines for the human care and use of experimental animals.

Vector Preparation

Pseudotyped AAV2/1 and AAV2/9 vectors were generated by packaging AAV2_based recombinant single-stranded (ss) and self-complementary (sc) genomes in AAV1 and 9 capsids. Briefly, the vectors were produced using a helper-virus free three-plasmid transfection in HEK293 cells with (1) the adenovirus helper plasmid (2) the AAV packaging plasmid encoding the rep2 and cap1 or 9 genes (pLTRC02 for AAV1 and p5E18-VD2/9 for AAV9) (3) the AAV2 vector plasmid containing mSeAP or GFP (under control of the cytomegalovirus immediate early (CMV IE) promoter) as ss or sc genome (Xiao, Li et al. 1998). This latter plasmid was constructed by deleting the D sequence and the terminal resolution site (trs) site from one of the inverted terminal repeat. The recombinant vectors were purified by double-CsCl ultracentrifugation followed by dialysis against phosphate-buffered saline. Physical particles were quantified by real time PCR for vectors injected in mice and by dot blot hybridisation for vectors injected in kittens and the vectors titers were expressed as viral genome per milliliter (vg/ml).

In Vivo Injection of the AAV Vectors

Neonates mice were injected on the day of birth (post natal 1, PN1). For i.m. injections, AAV vector solutions (ssAAV2/1 (n=2), ssAAV2/9 (n=2), scAAV2/1 (n=2) or scAAV2/9 (n=3) encoding mSeAP or GFP were injected into both triceps and gastrocnemius muscles (1 injection site per muscle, 5 µl per injection, $8 \times 10^{+9}$ to $2 \times 10^{+10}$ viral genome per mouse). For i.p. injections, the viral solutions (ssAAV2/1, n=2, ssAAV2/9, n=1, scAAV2/1, n=1 and scAAV2/9, n=2) encoding mSeAP or GFP were injected into the peritoneal cavity of one day old C57Bl/6 mice (100 µl, $3 \times 10^{+10}$ to $10^{+11}$ viral genome per mouse). For i.v. injections, one day old C57Bl/6 mice were injected into the temporal vein with scAAV2/9-GFP vector (50 µl, 1.5×10+10 viral genome per mouse, n=3). Adult C57Bl/6 mice were injected into the tail vein with scAAV2/9-mSeAP or scAAV2/9-GFP vector (500 µl, $3 \times 10^{+11}$ vg per mouse, n=3).

At 2 days after birth, a total of $1.5 \times 10^{+12}$ vector genome-containing particles of scAAV9-CMV-eGFP were injected into the jugular vein of one SMA-affected kitten and one SMA-heterozygous kitten.

Perfusion and Tissue Processing for Histology

Muscles, brains and spinal cords were removed at 1 (PN2), 3 (PN4) or 7 (PN8) days post-injection from neonate mice or 7 and 35 days post-injection from adult mice. Adult C57Bl6 mice were anesthetized (xylazine 10 mg/kg, ketamine 100 mg/kg) and perfused intracardially with 0,1 M phosphate-buffered saline (PBS) followed by 4% paraformaldehyde (PFA) in PBS. Tissues were removed and post-fixed for 4 h in the same solution before being transferred overnight at 4° C. into 15% sucrose for brains and muscles and 30% sucrose for the spinal cords. Neonates were decapitated and tissues were immersed in 4% PFA for 4 h before being cryoprotected overnight at 4° C. Samples were frozen in cold isopentane (−50° C.) and serial sections were cut in a cryostat and stored at −80° C. for further analysis.

At 10 days post-injection, kittens were anesthetized (medetomidine 150 µg/kg, ketamine 10 mg/kg) and perfused transcardially with 10 ml of phosphate-buffered saline followed by 100 ml of 4% PFA. Brains and spinal cords were removed and cut into coronal 5 mm slabs then postfixed in 4% PFA following by overnight cryoprotection in 30% sucrose and then frozen on dry ice in OCT compound. Spinal cord slices were cut in intervalls of 1×100 µm followed by 5×10 µm in a cryostat. Hundred µm-thick sections were used for examination of GFP signal by confocal microscopy, and 10 µm-thick sections were used for immunocytochemistry.

Evaluation of Transgene Expression

For mSeAP histochemistry, muscles, brains and spinal cords from neonate mice were removed at 1, 3 and 7 days p.i., frozen in cold isopentane (−50° C.), and maintained at −80° C. for extemporal use. Brain and spinal cord from adult animals were harvested at 35 days p.i and treated under the same conditions. Tissue sections of 16 µm thick for brain and spinal cord, and 8 µm thick for muscles were performed in a cryostat and subsequently processed for transgene expression. The sections were fixed with 0.5% glutaraldehyde, washed with PBS and endogenous alkaline phosphatase was heat-inactivated for 30 min at 65° C. Sections were then incubated overnight at 37° C. in 0.165 mg/ml 5-bromo-4-chloro-3-indolylphosphate and 0.33 mg/ml of nitroblue tetrazolium in 100 mM Tris-HCl, 100 mM NaCl and 50 mM MgCl2, counterstained with hematoxylin-eosin, and mounted with Eukit.

For GFP immunohistochemistry in mice, sections were washed in PBS and incubated for 30 min in a solution of hydrogen peroxide (Peroxydase-Blocking solution, Dako) for inhibition of the endogenous peroxidases. After washing in PBS, sections were blocked for one hour at room temperature in PBS with 10% goat serum (Dako) and 0.4% Triton and then incubated overnight with a rabbit polyclonal anti-GFP (Abcam; 1:3000). A biotin-conjugated secondary antibody (Vectastain, 1:200) and the Vectastain Elite ABC kit were used, and DAB staining was revealed with the DAB substrate kit for peroxydase (Vector Laboratories). Sections were dehydrated in alcohol and xylen, and mounted with Eukit.

GFP immunocytochemistry in cat was realised on 10 µm spinal cord frozen sections. Briefly, spinal cord sections were permeabilized with 0.2% Tween 20 in PBS (pH 7.4), blocked with 5% goat serum, incubated two nights at 4° C. with polyclonal antibody AB3080 to GFP (Chemicon, 1:50) and incubated with a biotinylated goat anti-rabbit antibody. The immunolabeling was revealed after an incubation with the streptavidine-peroxydase complex by using the diaminobenzidine substrat peroxydase. The sections were counterstained with haematoxylin.

Motor neuron's choline acetyltransferase was labeled with choline acetyltransferase (ChAT) goat polyclonal ChAT antibody (AB144P, Chemicon, France, 1:100). Briefly, spinal cord sections were blocked with 1% rabbit serum in PBS/Tx100 0.4%, incubated one night at room temperature with the primary antibody and incubated with a biotinylated rabbit anti-goat antibody. The immunolabeling was revealed after an incubation with streptavidine alexa 555 fluor and sections were coverslipped with Mowiol medium (Calbiochem, USA) to be viewed under confocal microscopy.

Laser Confocal Scanning Microscopy

GFP expression and immunocytochemistry were observed with an inverted Nikon TE-2000 laser scanning confocal microscope, equipped with a blue argon ion laser and a helium neon laser emitting monochromatic rays at 488 nm (green) and 543 nm (red), respectively. Slides were scanned serially using a water immersed X20 objective. Each image was recorded in a separated channel (channel green for GFP and channel red for streptavidin 555) and overlayed to allow detection of colocalized fluorescent signals.

Example 1

Intramuscular Injection of mSEAP-expressing AAV Vectors in the Neonatal Mouse

We first evaluated the potential of serotype 1 and 9 ss- or scAAV vectors to transduce the CNS cells after i.m. injection. The ssAAV1, ssAAV9, scAAV1 or scAAV9 encoding the murine secreted alkaline phosphatase (mSEAP) under the cytomegalovirus (CMV) promoter were injected into both triceps and gastrocnemius muscles in one day old C57Bl6 mice (8.10+9 to 2.10+10 viral genome per mouse, 3 mice per group). The injected muscle, brain and spinal cord tissues were removed 1, 3 or 7 days post injection and analysed for mSEAP expression using histochemistry.

The mSEAP expression was detected in the injected muscles 3 and 7 days after injection of each AAV serotype, except with ssAAV9, the expressing level dramatically increasing with time (FIG. 1a). In the CNS, transgene expression was detected only after i.m. injection of scAAV9. Interestingly, the mSEAP expression was detected in the epithelial cells of the choroids plexus (FIG. 1b), which have a crucial role in the secretion and the clearance of many proteins and toxins in the cerebrospinal fluid (CSF) (Redzic, 2005). The mSEAP expression in the choroids plexus was found as soon as 3 days post-injection (PN4), and the expression levels again increased with time. A weak transgene expression was also located in and around blood vessels of the brain and the spinal cord after i.m. injection of the scAAV9 vector (FIG. 1c).

Example 2

Intraperitoneal Injection of mSEAP-expressing AAV Vectors in the Neonatal Mouse

We then analysed whether i.p. administration of ssAAV1, ssAAV9, scAAV1 and scAAV9 in one day old C57Bl6 mice (100 µl, $3.10^{+10}$ to $1.10^{+11}$ viral genome per mouse) could mediate transgene expression in the CNS at 1, 3 or 7 days post injection.

A low level of mSEAP expression was detected in the diaphragm muscle fibres of mice injected with ssAAV1 by 3 days post-injection, which was similar to that observed with scAAV1 (FIG. 2a), and with both vectors at 7 days after injection. (FIG. 2a). SsAAV9 transduce a few muscle fibres only at 21 days post injection, whereas an intense mSEAP staining was found in the diaphragm when using scAAV9 from 3 days post-injection (FIG. 2a). This high level of transduction was also observed in other muscles such as the triceps brachii or gastrocnemius muscle (data not shown).

The epithelial cells of the choroids plexus and the ependyma appeared clearly labelled after injection with scAAV9 (FIG. 2b). A robust transduction was further observed in these regions at 7 days post-injection (FIG. 2b). Transgene expression was also observed within the meninges and blood vessels at 7 days post-injection, both in the brain and throughout the spinal cord, and was higher than that observed after i.m. injection (FIG. 2c). Interestingly, mSEAP expression was also detected in some neural cells in the brain and the spinal cord (FIG. 2d). Taken together, these results indicate that i.m. or i.p. injected scAAV9 vectors that express the mSEAP protein can efficiently target the CNS, especially the epithelial cells of the choroids plexus and the ependyma.

Example 3

Transgene Expression in the CNS After i.m. or i.p. Injection of scAAV9-GFP in the Neonatal Mouse Since mSEAP is a secreted protein, the transgene expression observed in the CNS cells after peripheral AAV injection could result from protein transcytosis rather than from AAV cell transduction. We thus verified whether similar results could be obtained when using a non-secreted protein.

A recombinant scAAV9 vector expressing the "green fluorescent protein" (GFP) was injected in neonatal mice either intraperitoneally (3.10+10 vg per mouse, 100 µl) or intramuscularly (8.10+9 vg in 20 µl per mouse, 5 µl per muscle). Seven days later, and similarly to that observed with scAAV9-mSEAP, the GFP expression was observed in the choroids plexus and ependyma cells located in the brain ventricles (FIG. 3a and FIG. 4a). Furthermore, we found in this case many GFP-positive neural cells in several brain regions located, in particular, close to the ventricles. Cell bodies and fibres in the hippocampus (FIG. 3b), the septum (FIG. 4b,c) and the entorhinal cortex (FIG. 3c, FIG. 4d-e) appeared efficiently transduced.

Importantly, GFP expression was detected in cells of the spinal cord at 7 days after AAV administration, including in cells with a motor neuron-like phenotype (FIG. 3d,e). A strong GFP expression was also found in fibres of the corticospinal tract that cross at the cervical spinal cord level (FIGS. 3f and 4h). Transduction of these fibres likely results from targeting of the upper MNs whose somas are located in the motor cortex and which also appeared GFP-immunopositive (FIG. 3d). Globally, a higher number of GFP-immunopositive cells were detected in the CNS after i.p. than after i.m. injection, due to either the difference of efficacy between the routes of injection or to the higher titre of vector used in the i.p. procedure.

Example 4

Transgene Expression in the CNS After Intravenous Injection of GFP-expressing scAAV9 in the Neonatal Mouse Since recombinant scAAV9 vector appeared as the most efficient one for mediating CNS cell transduction after i.m or i.p delivery, we evaluated whether this could be improved by using the i.v. route of administration.

GFP-expressing scAAV9 vectors were thus injected into the temporal vein of one day old C57Bl6 mice (50 µl, 1,5.10+10 viral genome per mouse) and the CNS tissues were removed and processed for immunostaining 7 days thereafter. A strong GFP expression was detected in both the choroids plexus and ependyma cells (FIG. 5a) and in the brain blood vessels (FIG. 5c). Again, we found GFP expression within cells of both neuron-like and glial-like phenotype throughout the brain, in particular in the entorhinal cortex (FIG. 5d) and the hippocampus (FIG. 5e,f).

A very high level of transgene expression was found throughout the spinal cord (from the cervical to the lumbar segments) in cells with a motor neuron-like phenotype and location (ventral spinal cord) (FIG. 5h-i). This probably results from diffusion of the vector through the blood vessels from the circulation to the brain parenchyma, or/and to axonal anterograde transport from upper CNS regions.

We then determine whether ssAAV9 could also cross the BBB and transduce the CNS cells after i.v. delivery, or if this property is specific to the double-stranded genome. In this aim, GFP-expressing ssAAV9 vectors were injected into the temporal vein of neonatal mice and GFP expression was analyzed 3 weeks after (in order to permit genome conversion into double-stranded DNA). Similar to that observed with scAAV9, ssAAV9-GFP proved to mediate CNS cell transduction after i.v. delivery, although its efficacy was lower than that of scAAV9. Again, the choroids plexus and ependyma cells expressed large amounts of GFP and many brain regions close to the cerebral ventricles were found to be transduced (FIG. 6a). For example, GFP-positive neurons were detected in the hippocampus and the habenular nuclei (FIG. 6a) and in the median eminence (FIG. 6b). Interestingly, some motor neuron-like cells were found to express GFP in the ventral spinal cord (FIG. 6c-e). A few CNS cells were also found to express GFP after i.m. or i.p. delivery of the recombinant ssAAV9 (data not shown).

Altogether, these data suggest an unexpected ability of serotype 9 AAV vectors —either conventional or self-complementary—to cross the BBB and transduce the CNS cells in neonatal mice, including the lower motor neurons, after a single intravenous injection in the neonatal mouse Example 5

Intravenous Injection of ss and scAAV9 Vectors in the Adult Mouse

Since the BBB is incompletely formed in neonatal mice, we evaluated whether the ability of the AAV9 vectors to transduce neural cells in newborn mice was preserved in adult mice. Ss and sc AAV9 vectors encoding for mSEAP ($3.10^{11}$ vg or $1.10^{12}$ vg per mouse) were injected into the tail vein of adult mice and transgene expression in the CNS was analyzed four weeks thereafter. After i.v. delivery of scAAV9-mSEAP, a sustained expression of the transgene was found in many brain regions such as the median eminence (FIG. 7f), the hippocampus (FIG. 7g) or the corpus callosum (FIG. 7h).

Importantly, there were many mSEAP-positive cells and fibers throughout the spinal cord after i.v. delivery of recombinant serotype 9 AAV vectors (FIG. 8a-g). Again, a higher level of transgene expression was observed with the sc- than with the conventional ssAAV9 vector (FIG. 8a,b versus 8c-g).

Similar injections using scAAV9-GFP demonstrated the superiority of scAAV9 for systemic gene delivery to the spinal cord. A high number of was found to express four weeks after i.v. injection of $2 \times 10^{12}$ vg scAAV9, GFP was expressed in the spinal cord in both neuronal and glial cells, as demonstrated using immunostaining of the glial fibrillary acidic protein (GFAP), a marker of astrocytes (FIG. 11).

Hence, our results show an efficient transduction of the CNS cells, including lower MNs and glial cells, after intravenous delivery of recombinant AAV9 vectors in adult mice in which the BBB is completely formed. This emphasizes the particular property of these vectors to pass from the circulation to the CNS parenchyma through the BBB, achieving widespread gene transfer to the nervous cells.

Example 6

Intravenous Injection of AAV9-GFP in a Large Animal Model

A validation of this new CNS gene transfer strategy in large animal models is a prerequisite to a potential application in human clinics.

We evaluated transgene expression in the spinal cord of LIX-1 kittens following intravenous delivery of recombinant scAAV9 vectors. Two days old kitten (one LIX-1 homozygous and one heterozygous) were injected into the jugular vein with GFP-expressing scAAV9. Ten days after, spinal cord tissue sections were analyzed for GFP expression using laser scanning confocal microscopy.

A strong GFP signal was observed along the spinal cord from the cervical part to the cauda equina both in the gray and white matter, the expression pattern appearing similar in both the heterozygous and affected animals. Nerve fibers of the fasciculi gracilis and cuneatus dorsal sensory tracts expressed high levels of GFP (FIG. 9a). Moreover, GFP expression was detected in a number of cell bodies in the ventral spinal cord, after both observation of GFP fluorescence (FIG. 9a,c) and immunohistochemical analysis (FIG. 9b-d). A double-immunostaining analysis using antibodies against GFP and choline acetyl transferase (ChAT) showed that, in both SMA-affected and non-affected kitten, a significant part of the GFP-positive cells were motor neurons (FIG. 10).

REFERENCES

Azzouz, M., A. Hottinger, et al. (2000). "Increased motoneuron survival and improved neuromuscular function in transgenic ALS mice after intraspinal injection of an adeno-associated virus encoding Bcl-2." Hum Mol Genet 9(5): 803-11.
Azzouz, M, et al., (2004). " Lentivector-mediated SMN replacement in a mouse model of spinal muscular atrophy." J Clin Invest. 114(12):1726-31
Boillee, S., K. Yamanaka, et al. (2006). "Onset and progression in inherited ALS determined by motor neurons and microglia." Science 312(5778): 1389-92
Cearley, C. N. and J. H. Wolfe (2006). "Transduction characteristics of adeno-associated virus vectors expressing cap serotypes 7, 8, 9, and Rh10 in the mouse brain." Mol Ther 13(3): 528-37.
Daly, T. M., C. Vogler, et al. (1999). "Neonatal gene transfer leads to widespread correction of pathology in a murine model of lysosomal storage disease." Proc Natl Acad Sci USA 96(5): 2296-300.
Fu, H., J. Muenzer, et al. (2003). "Self-complementary adeno-associated virus serotype 2 vector: global distribution and broad dispersion of AAV-mediated transgene expression in mouse brain." Mol Ther 8(6): 911-7.
Fyfe, J. C., M. Menotti-Raymond, et al. (2006). "An approximately 140-kb deletion associated with feline spinal muscular atrophy implies an essential LIX1 function for motor neuron survival." Genome Res 16(9): 1084-90.
Inagaki, K., S. Fuess, et al. (2006). "Robust systemic transduction with AAV9 vectors in mice: efficient global cardiac gene transfer superior to that of AAV8." Mol Ther 14(1): 45-53.
Kaspar, B K, et al. (2003). "Retrograde viral delivery of IGF-1 prolongs survival in a mouse ALS model." Science 301: 839-42.
MacLean, H. E., G. L. Warne, et al. (1996). "Spinal and bulbar muscular atrophy: androgen receptor dysfunction caused by a trinucleotide repeat expansion." J Neurol Sci 135(2): 149-57.
McCarty, D. M., H. Fu, et al. (2003). "Adeno-associated virus terminal repeat (TR) mutant generates self-complementary vectors to overcome the rate-limiting step to transduction in vivo." Gene Ther 10(26): 2112-8.
Monani, U. R. (2005). "Spinal muscular atrophy: a deficiency in a ubiquitous protein; a motor neuron-specific disease." Neuron 48(6): 885-96.
Pasinelli, P. and R. H. Brown (2006). "Molecular biology of amyotrophic lateral sclerosis: insights from genetics." Nat Rev Neurosci 7(9): 710-23.
Passini, M. A. and J. H. Wolfe (2001). "Widespread gene delivery and structure-specific patterns of expression in the brain after intraventricular injections of neonatal mice with an adeno-associated virus vector." J Virol 75(24): 12382-92.
Scherrmann, J. M. (2002). Drug delivery to brain via the blood-brain barrier. Vascul Pharmacol. 38: 349-54.
Xiao, X., J. Li, et al. (1998). "Production of high-titer recombinant adeno-associated virus vectors in the absence of helper adenovirus." J Virol 72(3): 2224-32.

The invention claimed is:

1. A method for delivering a gene of interest across the blood-brain barrier and expressing said gene of interest in spinal cord motor neurons or glial cells of a human subject, said method comprising:
   intravenously or intra-arterially administering an effective amount of a recombinant double-stranded self-complementary human serotype 9 adeno-associated virus (AAV9) vector comprising a gene of interest to said human subject,
   said administration allowing said vector to cross the blood-brain barrier and allowing expression of said gene of interest in spinal cord motor neurons or glial cells of said human subject,
   wherein said method is performed in the absence of a blood-brain barrier disrupting agent.

2. The method of claim 1, wherein said human subject suffers from a disorder of the central nervous system selected from the group consisting of spinal muscular atrophy and amyotrophic lateral sclerosis.

3. The method of claim 1, wherein the vector is a pseudotyped AAV vector.

4. The method of claim 1, wherein the vector comprises a replication defective AAV genome lacking functional Rep and Cap coding viral sequences.

5. The method of claim 1, wherein the gene of interest encodes a protein selected from the group consisting of growth factors, cytokines, hormones, neurotransmitters, enzymes, anti-apoptotic factors, and angiogenic factors.

6. The method of claim 1, wherein the vector is a pseudotyped AAV vector comprising an AAV2-derived genome packaged in an AAV9-derived capsid.

7. The method of claim 1, wherein expression of the protein in the vector is controlled by a ubiquitous, regulated or tissue-specific promoter.

8. The method of claim 1, wherein the gene encodes the survival of motor neuron (SMN) protein.

9. The method of claim 1, wherein said vector is administered by intravenous injection.

10. A method for delivering a gene of interest across the blood-brain barrier and expressing said gene of interest in spinal cord motor neurons or glial cells of a human subject, said method comprising:

intravenously or intra-arterially administering an effective amount of a recombinant double-stranded self-complementary human serotype 9 adeno-associated virus (AAV9) vector comprising a gene of interest to said human subject, said administration allowing said vector to cross the blood-brain barrier and allowing expression of said gene of interest in spinal cord motor neurons or glial cells of said human subject, wherein said method is performed without using mannitol as a blood-brain barrier disrupting agent.

11. The method of claim 10, wherein said human subject suffers from a disorder of the central nervous system selected from the group consisting of spinal muscular atrophy and amyotrophic lateral sclerosis.

12. The method of claim 10, wherein the vector is a pseudotyped AAV vector.

13. The method of claim 10, wherein the vector comprises a replication defective AAV genome lacking functional Rep and Cap coding viral sequences.

14. The method of claim 10, wherein the gene of interest encodes a protein selected from the group consisting of growth factors, cytokines, hormones, neurotransmitters, enzymes, anti-apoptotic factors, and angiogenic factors.

15. The method of claim 10, wherein the vector is a pseudotyped AAV vector comprising an AAV2-derived genome packaged in an AAV9-derived capsid.

16. The method of claim 10, wherein expression of the protein in the vector is controlled by a ubiquitous, regulated or tissue-specific promoter.

17. The method of claim 10, wherein the gene encodes the survival of motor neuron (SMN) protein.

18. The method of claim 10, wherein said vector is administered by intravenous injection.

* * * * *

(12) EX PARTE REEXAMINATION CERTIFICATE (11660th)
United States Patent
Barkats

(10) Number: US 9,926,574 C1
(45) Certificate Issued: *Mar. 19, 2020

(54) WIDESPREAD GENE DELIVERY TO MOTOR NEURONS USING PERIPHERAL INJECTION OF AAV VECTORS

(75) Inventor: Martine Barkats, Charenton le Pont (FR)

(73) Assignees: GENETHON, Evry (FR); CENTRE NATIONAL DE LA RECHERCHE SCIENTIFIQUE, Paris (FR)

Reexamination Request:
No. 90/014,290, Apr. 19, 2019

Reexamination Certificate for:
Patent No.: 9,926,574
Issued: Mar. 27, 2018
Appl. No.: 12/734,016
PCT Filed: Oct. 3, 2008
PCT No.: PCT/EP2008/063297
§ 371 (c)(1),
(2), (4) Date: Apr. 9, 2009
PCT Pub. No.: WO2009/043936
PCT Pub. Date: Apr. 9, 2009

( * ) Notice: This patent is subject to a terminal disclaimer.

(30) Foreign Application Priority Data

Oct. 5, 2007 (EP) .................................. 073014359

(51) Int. Cl.
*C12N 15/86* (2006.01)
*A61K 48/00* (2006.01)

(52) U.S. Cl.
CPC .............. *C12N 15/86* (2013.01); *A61K 48/00* (2013.01); *C12N 2750/14143* (2013.01); *C12N 2830/008* (2013.01)

(58) Field of Classification Search
None
See application file for complete search history.

(56) References Cited

To view the complete listing of prior art documents cited during the proceeding for Reexamination Control Number 90/014,290, please refer to the USPTO's public Patent Application Information Retrieval (PAIR) system under the Display References tab.

*Primary Examiner* — Sharon Turner

(57) ABSTRACT

The present invention relates to compositions and methods, in particular to methods based on systemic injection of rAAV, for delivering genes to cells of the central nervous system in mammals, such as brain neurons or glial cells, and in particular to motor neurons or glial cells of the spinal cord The invention also relates to methods of treating motor neuron disorders in mammals by expression of therapeutic genes. The invention stems from the unexpected discovery that peripheral injection of AAV vectors leads to a bypass of the blood brain barrier and a massive infection of motor neurons. The invention may be used in any mammal, including human subjects.

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1-18 is confirmed.

\* \* \* \* \*